(12) United States Patent
Wuchinich

(10) Patent No.: US 8,187,168 B2
(45) Date of Patent: May 29, 2012

(54) RETRACTABLE ULTRASONIC ENDOSCOPIC ASPIRATOR

(76) Inventor: David George Wuchinich, Yonkers, NY (US)

( * ) Notice: Subject to any disclaimer, the term of this patent is extended or adjusted under 35 U.S.C. 154(b) by 995 days.

(21) Appl. No.: 12/217,555

(22) Filed: Jul. 7, 2008

(65) Prior Publication Data

US 2009/0018490 A1    Jan. 15, 2009

Related U.S. Application Data

(60) Provisional application No. 60/958,783, filed on Jul. 9, 2007.

(51) Int. Cl.
*A61B 1/00* (2006.01)
*A61B 1/307* (2006.01)
*A61B 8/00* (2006.01)

(52) U.S. Cl. .................. 600/105; 600/135; 600/439

(58) Field of Classification Search .......... 600/105, 600/135, 439
See application file for complete search history.

(56) References Cited

U.S. PATENT DOCUMENTS

| | | | |
|---|---|---|---|
| 3,076,904 A | 2/1963 | Kleesattel at al. | |
| 3,323,785 A | 6/1967 | Mather | |
| 3,526,219 A * | 9/1970 | Balamuth | 600/565 |
| 3,589,363 A | 6/1971 | Banko et al. | |
| 4,063,557 A | 12/1977 | Wuchinich | |
| 4,223,676 A | 9/1980 | Wuchinich | |
| 4,425,115 A | 1/1984 | Wuchinich | |
| 4,493,694 A | 1/1985 | Wuchinich | |
| 4,750,488 A | 6/1988 | Wuchinich et al. | |
| 4,750,902 A | 6/1988 | Wuchinich et al. | |
| 4,922,902 A | 5/1990 | Wuchinich et al. | |
| 4,986,808 A | 1/1991 | Broadwin et al. | |
| 4,989,588 A * | 2/1991 | Kubota et al. | 606/2 |
| 5,169,397 A * | 12/1992 | Sakashita et al. | 606/27 |
| 5,176,677 A | 1/1993 | Wuchinich | |
| 7,449,004 B2 * | 11/2008 | Yamada et al. | 601/2 |
| 7,922,651 B2 * | 4/2011 | Yamada et al. | 600/104 |

(Continued)

OTHER PUBLICATIONS

Trademark Serial Number 71559611, Trademark Registration 514573, Inco Alloy International, Permanickel, Date of Status Apr. 3, 2010, Registration date Aug. 30, 1949, Retrieved from TARR web server, 3 pages.*

(Continued)

*Primary Examiner* — Thomas J Sweet
*Assistant Examiner* — Alireza Nia
(74) *Attorney, Agent, or Firm* — Connolly Bove Lodge & Hutz

(57) ABSTRACT

A surgical instrument comprising a sleeve, a electro-mechanical transducer containing a hollow passage for producing mechanical vibrations in response to a magnetic field, an ultrasonic horn mechanically connected to the transducer, containing a hollow passage communicating with that in the transducer, for amplifying the produced vibration such that dissection of biological tissue is produced and a tip having a hollow passage, mechanically connected to the horn and whose passage communicates with that in the horn, for contacting such tissue, connection of the passage to a source of vacuum and a sheath connected to the instrument and surrounding the tip and horn, with a connection to a source of irrigating fluid and a structure for mounting the transducer and horn within the sleeve permitting retracting and extension of the transducer and horn within and with respect to the sheath. The transducer, horn and tip are immersed in the irrigating solution. The instrument may also include a telescope for viewing the tissue contacting site and provision for electrifying the tip with electro-cauterizing current as well as provision for the use of endo-laser fulguration of the site.

15 Claims, 2 Drawing Sheets

U.S. PATENT DOCUMENTS

2003/0225332 A1* 12/2003 Okada et al. ............... 600/439
2004/0034340 A1* 2/2004 Biscup ...................... 606/1

OTHER PUBLICATIONS

Earl F. Nation—The development of the wire-loop resectoscope and the ensuing controversy concerning transurethral versus suprapubic Prostatectomy, Journal of Urology, V. 118 Jul. 1977, pp. 196-203.

Harry W. Herr—Epochs in Endourology, Journal of Endourology, vol. 20, No. 2, Feb. 2006, pp. 85-91.

Malloy et al, Bladder outlet obstruction treated with transurethral ultrasonic aspiration, J. Urology, vol. 37, No. 8, (Jun. 1991) pp. 512-515.

Urological and allied diagnostic instruments and high frequency equipment, American Cystoscope Makers, Inc., 1952, p. 118, 121.

* cited by examiner

RETRACTABLE ULTRASONIC ENDOSCOPIC ASPIRATOR

This application is based on U.S. provisional application No. 60/958,783 filed Jul. 9, 2007.

HISTORICAL INTRODUCTION AND PRIOR ART

Endoscopic surgery embraces a technique and instrumentation developed to remove unwanted tissue growths from within the human body through a natural orifice, such as the throat, nose, rectum, urethra and vagina. Because use of natural opening to perform surgery lessens the insult to tissue, patient morbidity is reduced and patient recovery hastened. The modern technique as applied to urological surgery is reported by Herr to have been developed in its essential elements in 1806 using hollow tubes and reflected candlelight to examine the bladder through the urethra. The introduction of optical lenses and electric lamps in the $19^{th}$ century greatly improved surgical vision and thus precision in excision, but the technique remained difficult to learn and use to remove prostatic tissue and did not compete with open surgical procedures for treatment of prostate enlargement or bladder tumors and stones.

Very substantial advances were made in the early $20^{th}$ century with the use of high frequency electrical current to cauterize and fulgurate bladder tumors. The nearly concomitant development of the glass relay lens telescope permitted an expansive view of the surgical site as well. Gradually, as Nation relates, successive incremental changes to the instruments resulted in one having a cutting electrode shaped like a loop to which was provided either interrupted or continuous high frequency electrical current for respectively either coagulating or cutting tissue. The action of the loop electrode was further enhanced by a mechanism that permitted axial movement within the tubular sheath of instrument. Thus the electrode could be advanced with respect to the rest of the instrument and moved independently of the telescope and other fixed elements within the surgical field to shave slivers of prostatic tissue or to sever the stalk of a bladder tumor.

After World War II, endoscopic surgery, as shown in an illustration provided by American Cystoscope, became the method of choice for removing bladder tumors and small to medium-sized enlarged prostate glands in urology. The instrument had become known as the resectoscope and its use was taught in most urological surgery residencies. Improvements in both the lens systems and lighting, occasioned by the development of fiber optics, have resulted today in an elegant surgical appliance, only truly appreciated in attempts at its improvement.

An improvement to the spring mechanism, also illustrated by American Cystoscope, which advances and retracts the cutting loop, was introduced by Iglesias. The use of a leaf, rather than a coil, spring provided facile activation and placed a minimal burden upon the muscles of the surgeon's hand in executing the procedure, which normally requires from 30 to 45 minutes to complete.

Endoscopic surgery, followed with antibiotic treatment, has greatly advanced the treatment for benign prostatic enlargement (BPH) and bladder tumors throughout the world. In 1994 188,000 such procedures were performed in the United States. Typically, patients are hospitalized for one to three days and can resume a normal life in a week or two. There remain, however, complications to the procedure that, while not common, do affect patient comfort and acceptance. Incontinence, or the inability to control urination sometimes occurs, as does impotence. In addition, because the bladder neck, which includes the internal sphincter, may be removed during the procedure on the prostate, following surgical recovery, during ejaculation the semen flows into the bladder rather than leaving the penis—a condition termed retrograde ejaculation. Perforations of the prostatic capsule, which encloses the gland and which normally remains intact after the procedure so that urine is entirely conveyed outside the body through the penis, also rarely occurs. The electric cutting current does not discriminate between elastic, fibrous capsule and the fleshy prostate. Care must be taken by the surgeon to direct the instrument away from this tissue, an accomplishment only experienced visual observation can provide.

The removal of the bladder neck is related to the surgical technique itself, as the loop is first advanced into tissue, electrified and then drawn toward the surgeon to excavate the prostatic gland—a movement termed antegrade resection, as the loop is only activated with current when moving toward the front of the patient. Using such an approach, the surgeon always has a clear view of the tissue he is removing, thereby reducing the chance of perforating the prostatic capsule.

Impotence is thought to result from possible damage to the nerves in the region of the penis by the electrical cutting current, or heating produced by the passage of this current through nerve tissue, but no definitive cause has yet been identified.

Incontinence can result from the removal of external sphincter, which controls actual urination, during the procedure. Again careful visual identification of this tissue is necessary to preclude this complication.

In an attempt to reduce the inherent hazard of electrosurgery, Wuchinich developed in 1988 an endoscopic instrument (U.S. Pat. No. 4,750,488; U.S. Pat. No. 4,750,902; U.S. Pat. No. 4,922,902) that excised tissue using ultrasonic vibration. This instrument relied upon the demonstrated ability of high intensity ultrasonic vibration to part tissue, as was amply demonstrated by his prior development of the ultrasonic aspirator for use in removing brain tumors and other neoplasms in a conventional open-site surgical procedure (U.S. Pat. No. 4,063,557; U.S. Pat. No. 4,223,676; U.S. Pat. No. 4,425,115). While the endoscopic instrument included a telescope and light source and was introduced into the prostate or bladder in exactly the same manner as the resectoscope, it contained a long, slender and hollow ultrasonic horn in place of the electro-surgical loop. When this horn was vibrated and brought into contact with tissue and suction applied to the bore of the horn, cores of tissue were excavated by the annular penetration of the end of the tip into tissue and withdrawn by the applied vacuum to a container. Excision thus did not involve the use of electric currents, but provision was made to electrify the ultrasonic cutting tip with coagulating current to control bleeding where necessary. Cutting current was not applied.

Ultrasonic surgery had been shown in neurosurgery to discriminate between tissues types. For example, it was found possible in neurosurgery to entirely remove a tumor from the spinal cord without any nerve dysfunction. Neural tissue contains far less intra-cellular water than many neoplasms and, as ultrasonic dissection is believed to rely upon cavitation, which is, in turn, directly related to the water content of tissues, this tissue is much less susceptible to its effect than are tissues with greater hydration. In a like manner, tumors were entirely excavated from the carotid artery, without damage to the arterial walls. Blood vessel walls are composed of fibrous elastic material and resistant to ultrasonic attack.

Unlike the principle of electro-surgery where the flow of current heats tissue to the boiling point of its water with the steam produced thus bursting cell walls, ultrasonic surgery does not produce an overall elevation in temperature during excision. No elevation in temperature was measured in the tissue or tip during tissue excision.

Because in-vivo experiments upon canine specimens showed that the prostate could be entirely enucleated and yet leave the capsule intact, it was thought the same benefit would enhance its use and safety in urology.

Malloy subsequently reported the successful use of this instrument on 69 patients in which bladder neck removal was completely avoided and, despite the adjunctive use of the resectoscope specifically for comparative pathologic assays of excavated tissue, his report recommended further investigation of a promising technology by the profession. However, medical and technical observers attending the surgical procedures noted that use of the instrument required more skill than a surgeon trained in endoscopic electroresection might feel, in some cases, comfortable in providing.

While all the benefits demonstrated by ultrasonic excision in neurosurgery were indeed conveyed in its use in urology, the instrument lacked one of the principal attributes of the well-developed and refined resectoscope: retractability of the cutting implement.

Whereas the loop could be advanced into and withdrawn from the surgical field, the tip of the hollow ultrasonic horn remained fixed in the field of view, obscuring vision of that portion of the surgical field it occupied. Very skillful surgeons were able to adjust to this deficit, but others were not and felt they could not see where they were going to cut. In addition, unlike the antegrade cutting action of the loop, use of the ultrasonic aspirator required it to be advanced into the tissue in a retro-grade direction, toward the back of the prostate. As surgeons were not convinced that the bladder capsule would resist the cutting action of the tip, despite evidence that it would, they were reluctant to bore into tissue when the proximity of the capsule was not known. The same fear had occasioned the use of the open site surgical aspirator until surgeons felt assured that no damage to blood vessel walls or nerve tissue would unintentionally result, and it was expected that, with use, such concerns would also subside in the urological application. Indeed, it is generally acknowledged that endoscopic electro-resection itself is one of the most difficult skills for urologists to acquire, as they must recognize anatomy though the limited visual field of the telescope. However, the fixed position of the tip within the surgical field remained a problem and it was felt this immobility would limit acceptance by the profession. In the ultrasonic instrument developed for this clinical investigation and described in the various patents granted Wuchinich, no way could be found to reliably and safely allow retraction and advancement of the tip without great complication and awkward modification to the design. To move the ultrasonic horn, not only the horn but also the ultrasonic transducer, to which it was firmly mechanically attached, had to be made mobile. Because high voltage electrical connections were made to the piezo-electric transducer, the transducer had to be sealed against any contact with irrigation fluid. Yet, the transducer, vibrating in unison with the horn to which it supplied vibrational power, induces seal failure through its own and very necessary vibration and put any attempt to ensure a hermetic environment in peril. Indeed, Wuchinich later invented and patented an ultrasonic endoscopic aspirator that permitted both rotation and retraction of the tip (U.S. Pat. No. 5,176,677), but this device required complicated sealing to prevent irrigation fluid from wetting the transducer, making the instrument difficult and expensive to manufacture.

OBJECTS AND ADVANTAGES

It is the object of this invention to permit the extension and retraction of the surgical tip with respect to the instrument containing the tip, such movement controllable by the operating surgeon. It also the object of this invention to provide a source of vibration that does not require direct electrical connection but instead utilizes a magnetic field, permitting the vibration source as well as all working features of the instrument, the irrigation and aspiration passages and the horn and tip, to be immersed in the irrigation fluid. It is a further object of this invention to use the irrigation fluid to cool the vibration source.

DRAWING FIGURES

REFERENCE NUMERALS IN THE DRAWINGS

Figure 1:
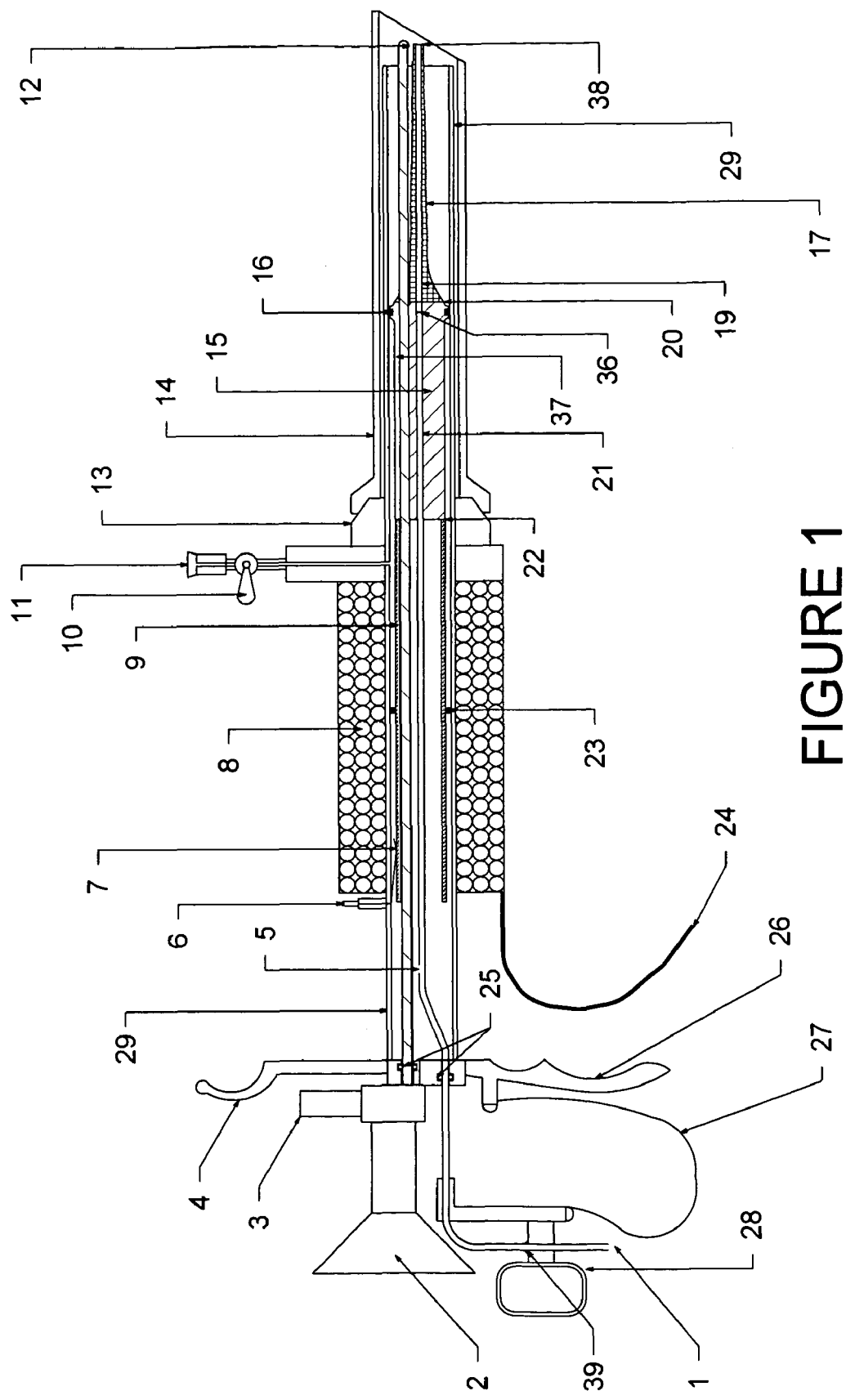
FIG. 1 is a drawing of the entire instrument showing every feature important to its operation.

1. Aspiration tube termination
2. Telescope
3. Connection to telescope light source
4. Finger grip
5. Transducer pre-aspiration orifice
6. Electro-cautery connection terminal
7. Electro-cautery sliding contact
8. Electric coil
9. Hollow transducer
10. Irrigation valve
11. Irrigation tubing connection
12. Telescope objective
13. Sleeve-sheath coupling
14. Sheath
15. Ultrasonic Horn
16. Coil spring sliding nodal horn support
17. Ultrasonic aspirating tip shown retracted
18. Not used in drawings
19. Aspiration passage
20. Horn-tip connection
21. Aspiration tube
22. Transducer-horn connection
23. Coil spring transducer nodal sliding support
24. Coil electrical connections
25. Seals
26. Finger grip
27. Leaf spring
28. Thumb grip
29. Sleeve
30. Spirally rolled magnetostrictive transducer
31. Transducer coupling face to horn
32. Acoustic joint between transducer and coupling face
33. Poisson decoupling slot
34. End caps
35. Transducer axis and hollow passage for telescope and aspiration tube.
36. Aspiration tube-tip joint
37. Horn slot
38. Tip opening 39. Aspiration tube-thumb grip attachment

DESCRIPTION

FIGS. 1-2

The difficulty in permitting axial movement of the ultrasonic transducer can be removed by replacing the piezo-electric transducer of the prior art with one using a hollow magnetostrictive transducer which requires no direct electrical connection and can safely withstand immersion in aqueous irrigating solutions. Kleesattel first disclosed a removable solenoid magnetostrictive transducer (U.S. Pat. No. 3,076,904). His design, elegant in its simplicity and function, was incorporated first into ultrasonic dental handpieces for the removal of plaque from teeth and then into Banko and Kelman's apparatus (U.S. Pat. No. 3,589,363), which formed the basis for the now universally practiced medical procedure of phaco-emulsification. It was also used in Wuchinich's ultrasonic surgical aspirator (U.S. Pat. No. 4,063,557; U.S. Pat. No. 4,223,676; U.S. Pat. No. 4,425,115), which found widespread acceptance in neurosurgery for the removal of brain tumors. However, these designs used a solid slender bar composed of layered thin magnetostrictive sheet material, such as permanickle. Broadwin and Rose (U.S. Pat. No. 4,986,808) later disclosed a magnetostrictive transducer having a central axial hole. Such an opening is desirable to permit passage of a telescope and to provide an aspiration pathway, but their design, using fins of magnetostrictive material radially positioned about the tubular hole, was intended for open site surgical procedures where retraction of the cutting tip is not required and it does not fully utilize the limited space available for transducer material in a resectoscope.

As shown in FIG. 1, which is a cross sectional view of the instrument, a hollow magnetostrictive transducer 9 is attached 22 to a hollow ultrasonic horn 15, which is attached 20 to a slender tip 17 having an open end for contacting, cutting and aspirating tissue. The attachments 22 and 20 may be made by any of the methods known to the art such as welding, brazing, screw threading, press-fitting or using adhesives. The horn 15 can also be removably attached 20 to a tip. Such attachments using screw threads are well known in the art. Both the transducer 9, attached horn 15 and tip 17 slide together within a sleeve 29 made of non-electrically conductive material. A telescope 2 and aspiration tube 21 run from one end of the sleeve 29 through the transducer and the horn 15. The aspiration tube is press fit or otherwise attached 36 to the opening in the tip 17 while a slot 37 in the horn accommodates passage of the telescope. The telescope then overlies the tip with its objective 12 located near the open end of the tip terminus 38.

Power to vibrate the transducer 9 is provided by an electric coil 8 positioned about the outside of the sleeve 29, which is made of non electrically conductive material. As the energy is transferred to the transducer by the magnetic field produced by the coil, and not by direct electrical contact, as is the case with piezo-electric transducers, this transducer is free to move axially within limits and yet receive power to vibrate. Thus the transducer/horn combination can be extended and retracted at will.

Axial motion is provided by supporting the transducer and horn within the sleeve 29 only at points of little or no ultrasonic motion, known as nodes. This method of support is described by Wuchinich in U.S. Pat. No. 5,176,677 and U.S. Pat. No. 4,750,902 for use in ultrasonic surgical instruments and is well known in the art and hereby incorporated herein by reference. The coil spring supports 23 for the transducer and 16 for the horn permit axial movement of the transducer-horn-tip combination while not impeding the flow of irrigation fluid over the tip or about the transducer. This form of support, as described in U.S. Pat. No. 3,323,785, consists of a coil spring joined to itself to form a toroidal spring stretched over the transducer or horn to elastically support the structures while allowing fluids to pass over the transducer and horn.

To provide an electro-cautery current to the tip, a connection 6 is provided for a source of electro-cauterizing current and connected to a sliding electrical contact 7 with the transducer 9. Certain magnetostrictive materials, such as PERMANICKEL (a trademark for a high nickel alloy), are electrically conductive and will convey such currents. The horn 15 and tip 17 can also be made of electrically conductive material, such as 6A1-4V titanium, so that this current can be made available at the tissue-excising open end of the horn.

The telescope 2, releasably fitted and retained within the sleeve 29 utilizing any of the several methods common in the design of endoscopes, is typically of the conventional relay lens type having a typical shaft diameter of 4 millimeters and integral fiber-optic illumination cable. Irrigating fluid, supplied from a container positioned above the patient, is admitted through a valve 10 to the inside of the sleeve by conventional lure-lock 11 connection. When the valve is opened the fluid flows through the sleeve and into the surgical site under gravity.

The telescope 2 and aspiration tube 21 are equipped with irrigation fluid seals 25 and the seal provided the aspiration tube also permits axial movement of the tube. Use of O-rings to provide such sealing and movement is well known in the art. The transducer/horn assembly is moved axially using the aspiration tube 21 to which it is attached 37. This tube is mechanically fixed 39 to the spring 27 loaded moveable component of an Iglesias thumb 39 and finger 4, 26 mechanism. Squeezing the thumb and finger grip together advances the transducer/horn assembly, while releasing the grips alls the spring 27 to retract the assembly.

The aspiration tube, terminating at 1 in the vicinity of the grip, is attached to a source of vacuum, commonly available in surgical operating rooms. Such simple attachments are well known in the art. This source may also be valved to initiate and terminate applied vacuum upon surgical demand.

The sleeve 29, which encloses the vibration source, horn and tip assembly, is surrounded by a removable metal sheath 14. This sheath is similar to that used with resectoscopes, attaching to the body of the instrument using a releasable spring catch. It is admitted into the prostatic gland or bladder using an obturator. This device is inserted into the sheath at the commencement of surgery. It contains a moveable tip that can be angled to negotiate the 90-degree bend in the urethra as it approaches the prostate. Once the sheath is in place within the anatomy, the obturator is removed and the instrument, containing all the elements of the invention, is inserted and locked in the sheath at coupling 13 using well-established fixtures intended for this purpose in endoscopy. The use of such devices is well known in endoscopy and in the practice of endo-urology.

Of particular interest in endosurgery is the circumference of the sheath, as the natural body orifice through which the instrument is introduced must often be dilated to accommodate the sheath. The smaller in circumference the sheath can be made, the less trauma is inflicted upon the tissues forming the orifice during insertion. FIG. 1 shows the invention is in its essential form with all functional components delineated for clarity. It is obvious to practitioners skilled in the art and viewing FIG. 1 that the circumference of sheath 14 can be reduced by changing its diameter just to the right of the joint 20 where the tip 17 is attached to the horn 15. So done, the sheath then need only enclose the telescope and the tip in that portion of its length that is inserted into the natural orifice, and thereby reduce the needed dilation of the orifice. Indeed, it is also obvious that the coupling 13 between the sheath 14 and the sleeve 29 can be moved just to right of joint 20 where the tip 17 attaches to the horn, thereby permitting use of a uniformly sized sheath of reduced size to produce less dilation. None of these modifications alter in any way the operation or function of the instrument.

Magnetostrictive transducers are known to generate significant heat in converting electrical energy into mechanical vibration and normally require cooling. This heat results both from the mechanical stress of vibration and from eddy currents if the magnetostrictive material is a metal. In the dental prophylactic scaling ultrasonic tool using Kleesattel's solenoid transducer design, cooling was provided by passing the tap water irrigation used for lavage first around the transducer. In Wuchinich's ultrasonic surgical aspirator a separate water circulating cooling supply was provided the transducer.

In this invention cooling is provided by the irrigation fluid, which is admitted to entire inner region of the sleeve, both that enclosing the horn 15 and tip 17 and that surrounding the transducer 9. Normally this fluid flows out through the open end of the sleeve into the surgical field. To pass a small portion of this flow in the other direction and about the transducer 9, an opening 5, much smaller than the inner diameter of the irrigation tube, is made as shown. As this tube is normally connected to a source of vacuum, some irrigation fluid is drawn through this opening to create a flow to cool the transducer. Because the aspiration opening 5 in the irrigation tube is much smaller than the open, tissue-excising, end of the tip the vacuum available for tissue dissection is not significantly diminished. Wuchinich in U.S. Pat. No. 4,493,694 discloses this method of redirecting a portion of the irrigating flow in a surgical instrument.

Figure 2:
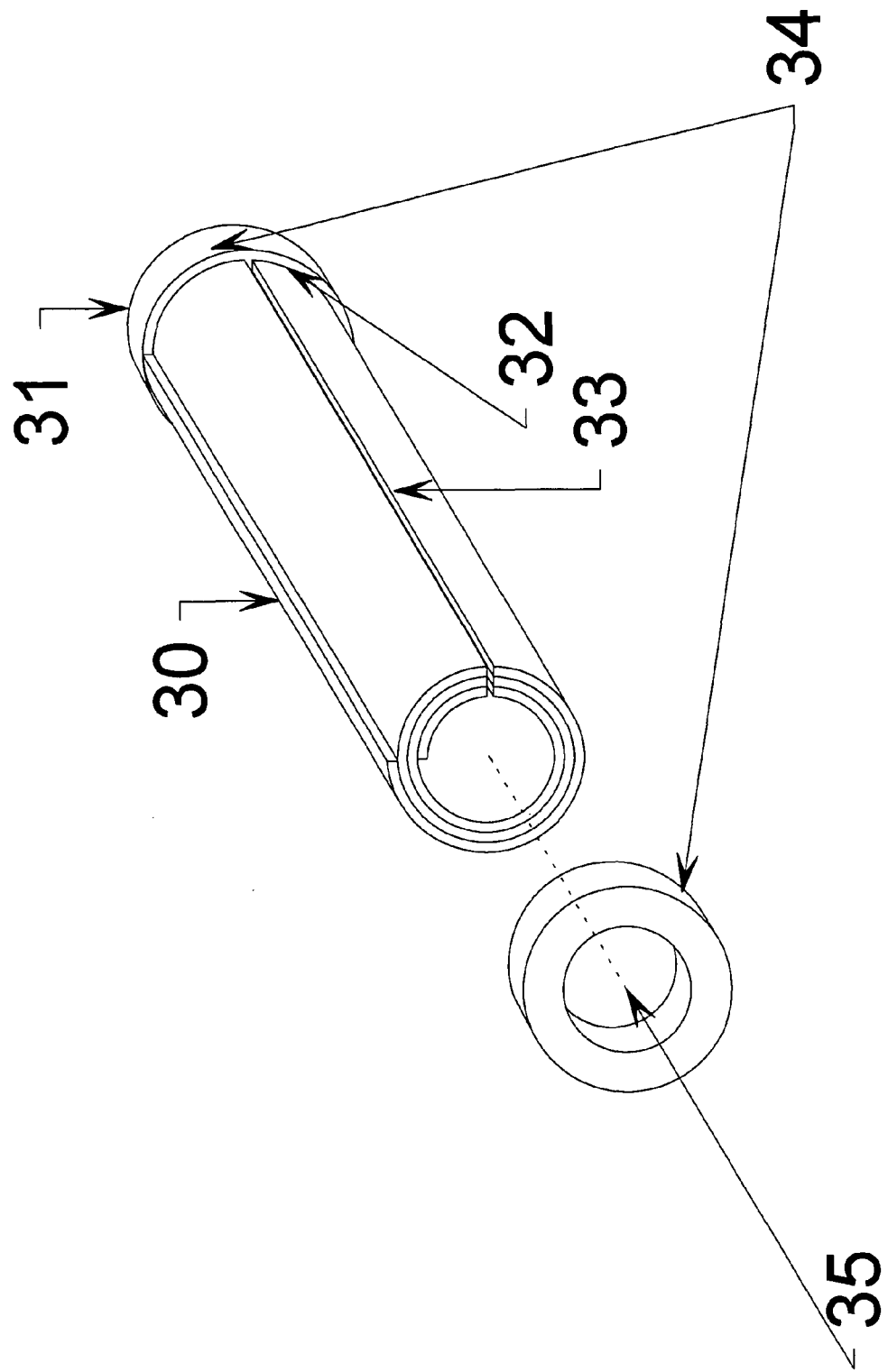
FIG. 2 is a drawing of the immersible magnetostrictive transducer, the preferred embodiment of the vibration source.

To fully utilize the space available for magnetostrictive material, and thus maximize the amount of vibrational power that can be provided in the restricted space of a resectoscope, the transducer is constructed of spirally rolled magnetostrictive sheet or of tubular ferro-ceramic (ferrite) material. FIG. 2 illustrates the construction if the magnetostrictive material is a metal, such as PERMANICKEL. A thin sheet of the material is required to minimize the heating produced by eddy currents generated in the metal by the magnetic field.

The rolled sheet is contained within two hollow end caps 34, which are attached 32 to the ends of the roll 30 using any of the methods available for making mechanical bonds, such as welding, brazing, soldering and adhesives. These caps, which prevent the spiral roll from unwinding, can be eliminated by just welding, brazing or other otherwise joining the edges of the roll. Once contained within the cap closures, the spiral roll 30 is slit axially 33 from its outer to inner surfaces. This slit interrupts circumferential Poisson coupled motion in the roll that always accompanies axial motion and ensures that the transducer produces principally axial motion, whose direction 35 is shown, when energized by the surrounding magnetic field. The sliding contact for conducting electrocautery current to the ultrasonic horn contacts the outer surface of the spirally rolled transducer 30. If a PERMANICKEL sheet is utilized to form the transducer an oxide is normally present on its surface. This oxide layer insulates the adjacent surfaces of the roll and prevents the production of eddy currents from circulating through its entire radial thickness. To establish electrical contact for application of the electro-cauterizing current, a strip of this oxide is removed from the outer roll surface.

One face 31 of one of the end caps is mechanically attached to the ultrasonic horn, again using any one of the forms of electrically conductive mechanical attachment, including adhesives, solder, welds, braze, press-fit, screw thread and self-locking luer that are known to those skilled in the practice of the art.

This invention discloses a preferred method of generating axially directed mechanical vibration for the purpose of removing tissue in surgical operations that permits independent movement of the ultrasonic components with respect to other elements of the invention, and as such it embraces all forms of providing such motion, including the use of resonantly vibrating component parts of the ultrasonic assembly. For example, the transducer can be designed to resonantly vibrate in the axial direction at a particular frequency and the ultrasonic horn can also be designed to vibrate in the same manner and at the same frequency. Methods for producing such designs are well known in the art. Furthermore, the horn can be composed of several horns, all joined integrally or releasably coupled together to provide increased length or an increase in vibration in the region of tissue contact.

The invention also includes other forms of ultrasonic motion that can be generated by magnetostrictive transducers and conveyed by ultrasonic horns, such as torsional, longitudinal-torsional and flexural motions.

Although electro-coagulating current is preferred for use in the surgical procedures using this invention, to those skilled in the art it is obvious that electro-cutting current can as well be applied to the horn without altering any elements described and disclosed.

It is also well known in the art that the invention also permits the use of laser coagulation by the incorporation within or about the telescope of a fiber optic channel to convey such coagulating illumination such as provided by the $CO_2$, KTP, PVP or Holmium lasers to the operative site.

I claim:

1. A surgical instrument comprises:
   a sleeve;
   a power source mounted outside of said sleeve for generating a magnetic field within said sleeve;
   an ultrasonic transducer in said sleeve, said transducer including a vibration source within said sleeve for generating mechanical vibrations in response to the magnetic field applied thereto by said power source, said vibration source being supported within said sleeve at a point where essentially no vibration occurs;
   a horn attached to said transducer operatively associated with and vibrated by said vibration source and supported within said sleeve at a point where essentially no vibration motion occurs;
   a tip operatively associated with said horn and vibrated by said horn, said tip having a terminus for extending outside of said sleeve and contacting tissue;
   said transducer with its said vibration source and said horn and said tip being longitudinally mounted within said sleeve for extending and retracting motion within said sleeve while said tip is vibrating independently of said sleeve, said extending and retracting motion being an axial movement which is relative to said power source;
   irrigating structure communicating with said sleeve for irrigating a work site having the tissue contacted by said tip and for irrigating said vibration source with fluid to contact said vibration source and the tissue;

aspiration structure communicating with said sleeve for withdrawing irrigation fluid and removed biological material from the tissue; and viewing structure for visualizing said tip and the tissue;

wherein said power source is an electric coil positioned about the outside of said sleeve, said sleeve being made of non-electrically conductive material, and the energy being transferred to said transducer by the magnetic field produced by said electric coil without direct electrical contact.

2. A surgical instrument of claim 1 where said vibration source is made of a high nickel alloy sheet material.

3. A surgical instrument of claim 1 where said vibration source is made of ferrite material.

4. A surgical instrument of claim 1 where said viewing structure includes a telescope.

5. A surgical instrument of claim 1 where said vibration source is made of permanickle a high nickel alloy sheet material.

6. A surgical instrument of claim 1 where said vibration source is made of ferrite material.

7. A surgical instrument of claim 1 where said viewing structure includes a telescope.

8. A surgical instrument of claim 1 where said transducer is constructed of a spirally rolled magnetostrictive sheet.

9. A surgical instrument of claim 1 where structure is in said sleeve for applying electro-cautery current to said tip.

10. A surgical instrument of claim 1 where said transducer is a layered magnetostrictive metal spiraled about a central hollow core.

11. A surgical instrument of claim 1 where said transducer is constructed of tubular ferro-ceramic material.

12. A surgical instrument of claim 10 where said vibration source is made of a high nickel alloy sheet material.

13. A surgical instrument of claim 11 where said vibration source is made of ferrite material.

14. A surgical instrument of claim 11 where said viewing structure includes a telescope.

15. A surgical instrument of claim 10 where said viewing structure includes a telescope.

\* \* \* \* \*